(12) United States Patent
Michael et al.

(10) Patent No.: US 6,613,332 B1
(45) Date of Patent: *Sep. 2, 2003

(54) ORAL ADMINISTRATION OF THERAPEUTIC PROTEINS

(75) Inventors: Jacob Gabriel Michael, Cincinnati, OH (US); Allen Litwin, Cincinnati, OH (US)

(73) Assignee: The University of Cincinnati, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/538,598

(22) Filed: Mar. 29, 2000

Related U.S. Application Data

(63) Continuation-in-part of application No. 08/947,551, filed on Oct. 11, 1997, now Pat. No. 6,174,529, which is a continuation of application No. 08/472,711, filed on Jun. 5, 1995, now abandoned, which is a division of application No. 08/329,685, filed on Oct. 26, 1994, now Pat. No. 5,609,871, which is a continuation of application No. 08/178,503, filed on Jan. 7, 1994, now abandoned, which is a continuation of application No. 07/994,932, filed on Dec. 22, 1992, now abandoned, which is a continuation-in-part of application No. 07/719,160, filed on Jun. 21, 1991, now abandoned.

(51) Int. Cl.[7] .................... A61K 39/00; A61K 9/16; A61K 9/48; A61K 31/70; A61K 39/12

(52) U.S. Cl. ............... 424/184.1; 424/497; 424/482; 424/422; 424/278.1; 424/207.1; 424/464; 424/451; 514/2; 514/8; 514/22; 514/23

(58) Field of Search ................. 424/184.1, 497, 424/482, 422, 278.1, 207.1, 464, 451; 514/2, 8, 22, 23

(56) References Cited

U.S. PATENT DOCUMENTS

| | | | |
|---|---|---|---|
| 4,016,254 A | 4/1977 | Seager et al. | |
| 4,017,647 A | 4/1977 | Ohno et al. | |
| 4,348,384 A | 9/1982 | Horikoshi et al. | |
| 4,469,677 A | 9/1984 | Michael et al. | |
| 4,507,276 A | 3/1985 | Tencza et al. | |
| 4,642,232 A | 2/1987 | Yman et al. | |
| 4,704,295 A | 11/1987 | Porter et al. | |
| 4,728,513 A | 3/1988 | Ventouras | |
| 4,774,226 A | 9/1988 | Lewenstein | |
| 4,798,844 A | 1/1989 | Fujita et al. | |
| 4,820,627 A | 4/1989 | McGeehan et al. | |
| 4,874,613 A | 10/1989 | Hsiao et al. | |
| 4,900,557 A | 2/1990 | Dell et al. | |
| 4,920,209 A | 4/1990 | Davis et al. | |
| 4,946,945 A | 8/1990 | Wojdani | |
| 4,981,693 A | 1/1991 | Higashi et al. | |
| 4,996,058 A | 2/1991 | Sinnreich et al. | |
| 5,019,384 A | 5/1991 | Gefter et al. | |
| 5,049,390 A | 9/1991 | Wojdani | |
| 5,171,568 A | 12/1992 | Burke et al. | |
| 5,202,159 A | 4/1993 | Chen et al. | |
| 5,230,888 A | 7/1993 | Baltimore et al. | |
| 5,236,713 A | 8/1993 | Wato et al. | |
| 5,286,493 A | 2/1994 | Oshlack | |
| 5,399,347 A | 3/1995 | Trentham et al. | |
| 5,591,433 A | 1/1997 | Michael et al. | |
| 5,609,871 A | 3/1997 | Michael et al. | |
| 5,629,001 A | 5/1997 | Michael et al. | |
| 5,783,193 A | 7/1998 | Michael et al. | |
| 6,174,529 B1 | 1/2001 | Michael et al. | |

FOREIGN PATENT DOCUMENTS

| | | |
|---|---|---|
| AU | 52792/90 | 3/1989 |
| CA | 1050358 | 3/1979 |
| CA | 1109796 | 9/1981 |
| CA | 2020654 | 1/1991 |
| EP | 0277741 | 8/1988 |
| EP | 319545 | 6/1989 |
| EP | 0603992 | 12/2000 |
| FR | 2723/849 | 8/1994 |
| JP | 01-287032 | 11/1989 |
| WO | WO90/04963 | 5/1990 |
| WO | WO92/06708 | 2/1992 |

OTHER PUBLICATIONS

Adorini et al., Springer Semin Immunopathol vol. 14, 187–199, (1992).

Alonso, "Controlled Release of Tetanus Toxoid From Poly-(Lactic/Glycolic Acid) Microspheres," Proceed. Intern. Symp. Control. Rel. Bioact. Mater. Controlled Release Society, Inc., vol. 19 pp. 122–123 (1992).

Chanock et al. "Immunization by selective infection with Type 4 adenovirus grown in human diploid tissue culture," JAMA 195(6):151–158 (1966).

Chemical Abstracts vol 96 p. 370 (1982).

Childers et al., Regional Immunology vol. 3(6), 289–296, 1990/1991).

Czerkinsky et al. "Induction and assessment of immunity at enteromucosal surfaces in humans: Implications for vaccine development" Clin. Infect. Dis. S106–113 (1993).

Davis et al., Microbiology, Third Edition, Chapter 67, p. 1270 (1980).

Eldridge, et al., "Controlled vaccine release in the gut–associated lymphoid tissues. I. Orally administered biodegradable microcapsules target to the Peyer's patches," J. Controlled Release 11:205–214 (1990).

(List continued on next page.)

Primary Examiner—Nita Minnifield
(74) Attorney, Agent, or Firm—Morrison & Foerster LLP

(57) ABSTRACT

An orally administrable therapeutic protein is provided by combining the therapeutic protein with a stabilizing agent in an aqueous solution. The solution is coated onto nonpareils and microencapsulated with a water emulsifiable enteric coating composition. The microcapsules are orally administered. The coating protects the protein as it passes through the stomach. Upon reaching the small intestines, the basic pH of the intestinal juices will dissolve the coating, allowing the protein to be released and induce antigen specific immune response which has the specificity of the native molecule. The stabilizing agent protects the therapeutic protein from denaturation during the encapsulation process.

11 Claims, 2 Drawing Sheets

OTHER PUBLICATIONS

Engvall et al., The Journal of Immunology vol. 109(1), 129–135, (1972).

Excerpts from *Structure and Development of the Immune System*, Chapter 2, pp. 29, 30–31.

Fox, Bio/Technology 12:128 (1994).

Fukumori, et al., Chem. Pharm. Bull. 36(12):4927–32 (1988).

Fukumori, et al., Chem. Pharm. Bull. 36(8):3070–78 (1988).

Gilligan, et al., Oral Vaccines: Design and Delivery, Int'l Journal of Pharmaceutics, vol. 75 pp. 1–24 (1991).

Haynes Science 260:1279–1286 (1993).

Lai "Design and evaluation of water based pseudo–latex enteinc coating systems," Diss. Abs. Int. 49(10B):4254 (1985).

Langer, et al., Science 249:1527–1533 (1990).

Litwin et al, J. Allergy Clin. Immunol. 100:30–8 (1997).

Manganaro et al. "Oral immunization: Turning fantasy into reality," Int. Arch Allergy Immunol. 103:223–233 (1994).

Michael, J. "The role of digestive enzymes in orally induced immune tolerance," Immunogical Invest 18:1049–1054 (1989).

Moldoveanu et al. "Oral immunization with influenza virus in biodegradable micorspheres," J. Infect. Dis. vol. 167 pp. 84–90 (1993).

Moldoveanu et al. Current Topics in Microbiol & Immunol. 146:91–99, (1989).

Mowat, Immunology Today vol. 8(3), 93–98, (1987).

Murray, et al., Aus. J. Hospital Pharm. 20(3):235–38 (1990).

Novak, et al., "Murine model for evaluation of protective immunity to influenza virus".

O'Hagan et al. "Biodegradable Microparticles as Oral Vaccines," Proceed. Intern. Symp. Control. Rel. Bioact. Mater., , Controlled Release Society, Inc., vol. 19 pp. 118–119 (1992).

O'Hagan et al., 1991, "Biodegradable microparticle as controlled release antigen delivery systems," Immunology 73:239–242.

O'Hagan. *Oral immunization and the common mucosal immune system* CRC Press, Inc. 1–24 (1994). Sandstrom et al, Drugs 34:372–390 (1987).

Sandstrom et al, Drugs 34:372–390 (1987).

Sayegh et al., Proc. Natl. Acad. Sci. USA vol. 89, 7762–7766 (1992).

Tamura et al. "Superior Cross–Protective Effect of Nasal Vaccination to Subcutaneous Inoculation with Influenza Hemagglutinin Vaccine," Eur. J. Immunol. 22: 447–481 (1992).

Waldman et al. "Secretory Antibody following oral influenza immunization," Am. J. Med. Sci. 292(6):367–71 (1986).

Waldman, Robert H., et al., "Age–Dependent Antibody Response in Mice and Humans Following Oral Influenza Immunization," Journal of Clinical Immjnology, vol. 7, No. 4, pp. 327–332 (1987).

Wheeler et al. "Immunogenicity in guinea pigs and tolerance in grass" Int. Arch. Allergy Appl. Immunol. 83(4):354–8 (1987).

Wheeler et al., Int. Arch. Allergy Appl. Immunol. 83(4):354–8 (1987).

Wilson et al. "Adjuvant Action of Chloera Toxin and Pertussis Toxin in the induction of IgA Antibody Response to Orally Administered Antigen".

Wong, "Development of Novel Oral Enteric–Coated Aquaculture Vigro Vaccines" (1990) (unpublished Ph.D. thesis, Oregon State University, available from UMI Dissertation Services).

Wong,. Diss. Abs. Int. 52(5B):2519 (1990).

Xu–Amano et al., "Selective Induction of Th2 cells in murine Peyer's Patches by Oral Immunization," International Immunology, vol. 4, No. 4, pp. 433–445.

ORAL ADMINISTRATION OF THERAPEUTIC PROTEINS

CROSS-REFERENCES TO RELATED APPLICATIONS

This application is a continuation-in-part of U.S. patent application Ser. No. 08/947,551, filed Oct. 11, 1997, now U.S. Pat. No. 6,174,529, which is a continuation of U.S. patent application Ser. No. 08/472,711, filed Jun. 5, 1995, now abandoned, which is a divisional of U.S. patent application Ser. No. 08/329,685, filed Oct. 26, 1994, now U.S. Pat. No. 5,609,871, which is a file wrapper continuation of U.S. patent application Ser. No. 08/178,503, filed Jan. 7, 1994, now abandoned, which is a continuation of U.S. patent application Ser. No. 07/994,932, filed Dec. 22, 1992, now abandoned, which is a continuation-in-part of U.S. patent application Ser. No. 07/719,160, filed Jun. 21, 1991, now abandoned.

BACKGROUND OF THE INVENTION

Oral administration of any therapeutic agent is always problematic relative to administration by injection. Whereas administration by injection necessarily delivers the intact therapeutic agent into the body and where need be into the direct situs where it is required, with oral administration it is critical that the therapeutic agent pass through the digestive tract and be absorbed into the body without destruction of the therapeutic agent.

With smaller drugs such as aspirin and the like, this is not a critical problem. However, with larger molecules particularly proteins denaturization is a significant problem.

As discussed in the parent application, prior attempts to administer immunologically active proteins via oral ingestion had been unsuccessful. Likewise oral administration of any therapeutic protein has been generally unsuccessful.

With such therapy if the protein administered is a foreign protein, it will have an immunological effect activating the immune system. Whereas when the protein is a native protein such as insulin (whether derived from animal sources or produced from genetically modified microorganisms) the protein does not activate the immune system but rather establishes a concentration in the blood. Other such human proteins which are not recognized by the immune system as foreign would of course include human growth factor, transforming growth factor beta. There are of course a wide variety of therapeutic proteins which are not recognized as foreign by the immune system. Such natural proteins can have a wide variety of effects on the human body.

SUMMARY OF THE INVENTION

The present invention is premised on the realization that an orally administrable therapeutic proteins can be formed by microencapsulating the protein with a coating which is insoluble under acid conditions and resistant to proteolytic digestion. Such conditions are encountered in the mammalian stomach and part of the small intestines. Preventing exposure to acid and proteolytic digestion preserves antigenic structure of the protein and its ability to immunize.

The present invention is further premised on the realization that by microencapsulating the protein under totally aqueous conditions without employing any nonaqueous solvents, the structure of the protein remains intact.

More particularly, the present invention is premised on the realization that the therapeutic proteins should be coated with an acid stable coating under totally aqueous conditions so that they can pass through the stomach without being digested and then released intact into the small intestines where they can exert their therapeutic and/or immunological activity.

In a preferred embodiment, the enteric coating is a water emulsion of ethylacrylate methylacrylic acid copolymer, or hydroxypropyl methyl cellulose acetate succinate (HPMAS).

The objects and advantages of the present invention will be further appreciated in light of the following detailed description and drawings.

DESCRIPTION OF THE SPECIFIC EMBODIMENTS

Figure 1:
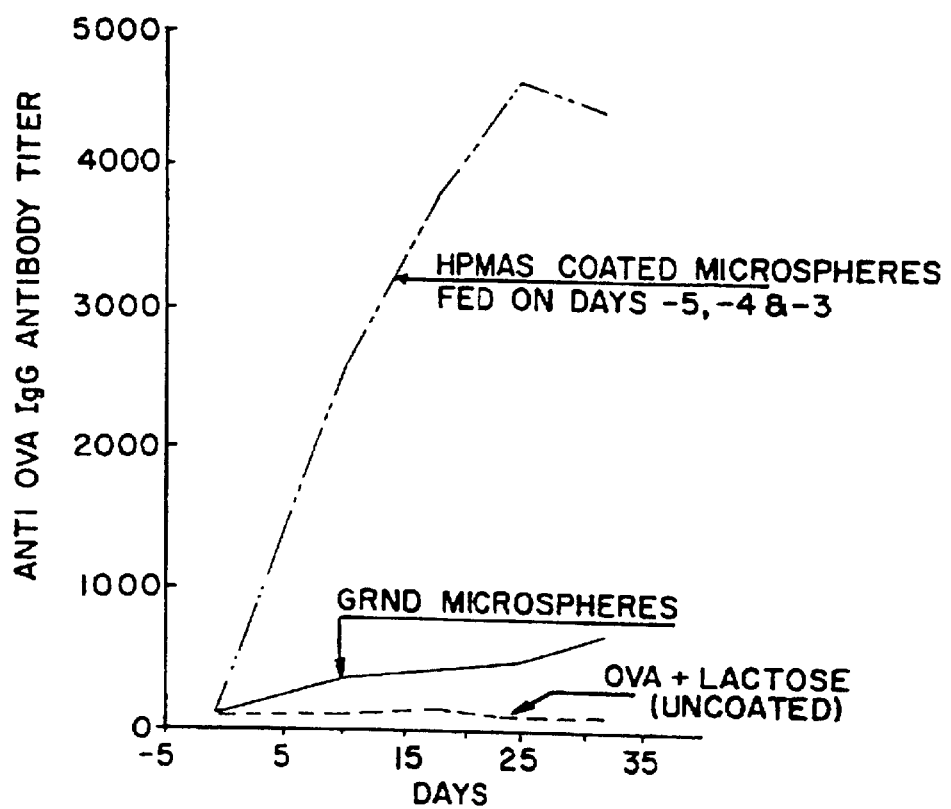
FIG. 1 is a graph depicting anti-OVA (hen egg albumin) IgG antibody titers of mice fed hydroxypropylmethyl cellulose acetate succinate (HPMAS) coated OVA containing microspheres or ground coated OVA microspheres or OVA in solution.

According to the present invention, an orally administrable therapeutic protein is formed by microencapsulating the therapeutic protein with an enteric coating.

The therapeutic proteins are dispersed in an aqueous solution. The aqueous solution is then sprayed onto nonpareils. Subsequently the microspheres are coated with a water emulsion of a polymer which upon solidification is acid resistant. This protects the therapeutic protein as it passes through the stomach and releases it into the small intestines where it can act upon the lymphoid tissue.

For the purpose of the present invention, therapeutic protein will include, for example, insulin, human growth factor, myelin basic proteins, collagen S antigen, transforming growth factor beta. These proteins are all human proteins or human protein analogs which are not recognized by the immune system as foreign. They have a physiological effect but do not necessarily activate the immune system. These proteins are generally available in lyophilized or ligand form.

A second component which can be added to the therapeutic protein is a stabilizing agent. Stabilizing agents provide physical protection for the protein. Generally these stabilizing agents are therapeutically inactive water soluble sugars such as lactose, mannitol and trehalose. These act to protect the therapeutic antigen during the coating process.

To form orally administrable microcapsules for use in the present invention, an aqueous solution of the therapeutic protein and the optional stabilizing agent is formed. The aqueous solution will include generally from about 0.5 to about 10% by weight of the therapeutic protein with about 1% being preferred, and from about 1% to about 10% by weight of the stabilizing agent with about 5% being preferred. If the protein solution has a low viscosity, it may be desirable to add 1–10% of polyvinylpyrrolidone to bind the therapeutic protein to the nonpareil.

Nonpareils are small, round particles of pharmaceutically inert materials. Generally nonpareils formed from the combination of sucrose and starch are preferred. One such brand is Nupareils which is sold by Ingredient Technology Corporation. The preferred size is 30–35 mesh.

The nonpareils are coated with an amount of the aqueous solution to provide a coating of 1–10% protein by weight on a solids basis. Glatt brand powder coater granulators such as the GPCG-1, GPCG-5, or GPCG-60 fluid bed coaters are suitable for use in this application. Coating conditions and times will vary depending on the apparatus and coating viscosity. But, generally all coating steps must be conducted at less than 50° C., preferably less than 35° C. to avoid denaturing the protein.

The protein coated microspheres are dried and subsequently coated with an acid stable polymer (enteric coating). Generally, the coating will be applied in the same manner as the protein with the same equipment.

The coating composition used in the present invention is preferably a water based emulsion polymer. The preferred coating is an ethylacrylate methacrylic acid copolymer sold under the trademark Eudragit L 30D manufactured by Rhom Pharma. This has a molecular weight of about 250,000 and is generally applied as a 30% aqueous solution. An alternate coating is hydroxypropylmethyl cellulose acetate succinate.

The coating composition can be combined with a plasticizer to improve the continuity of the coating. There are several well known plasticizers typically used. Triethylcitrate (TEC) sold by Morfley Inc. is preferred. This can form about 1–30% of coating composition. Although plasticizers can be liquid, they are not considered to be solvents since they lodge within the coating altering its physical characteristics. They do not act to dissolve the protein. Any plasticizer which dissolves or denatures the protein would be unacceptable.

Talc (3.0% of coating composition) can also be added to prevent sticking between the particles if desired. Also, an antifoaming agent (0.0025% of coating composition) such as sorbitan sesquioleate (Nikko Chemicals Company Limited) or silicone can be, added. Both the talc and antifoaming agent are added only if needed.

The microspheres coated with the therapeutic protein and optional stabilizing agents, are dried and are then coated with the enteric coating as previously described. The coating solution is about 30% polymer, 0–30% plasticizer, 0 to 3% talc and 0 to .0025% antifoaming agent and water. It is important that there be no organic solvents including alcohols and even glycols present in the coating composition. The presence of these solvents during coating application can denature the therapeutic protein. The coating is conducted in the same equipment used to coat the nonpareils with therapeutic protein. The temperature for this coating should be about 30° C. but less than 50° C.

In an alternate embodiment of the present invention, a therapeutically acceptable water dispersible aluminum compound such as aluminum sulfate or aluminum hydroxide are added to the aqueous dispersion or solution of protein prior to coating onto the nonpareil. This acts to increase immunogenicity of the proteins. Generally 1% to 10% of aluminum compound is added.

The enteric coated microspheres then can be placed in gel capsules for oral administration to humans. Dosage will depend on the individual and the course of the therapy. For example, in treatment with ragweed microspheres, the dosage would be 0.03 to 35 units in terms of a major allergenic protein, Amb a 1, administered daily. This is similar to the dosage provided by injection.

The invention will be further appreciated in light of these following examples.

EXAMPLE 1

Immunogenicity of Encapsulated OVA

Immunological properties of OVA released from microspheres were tested following oral administration to 6–8 weeks old BDF mice. Control groups of mice were fed with unencapsulated OVA (OVA and lactose) or ground enteric coated microspheres. The enteric coating was hydroxy propyl methyl cellulose acetate succinate sold by Shin Etsu Chemical Company which was applied in an aqueous suspension. (10% HPMCAS, 2.8% TEC, 3.0% talc, 0.0025% Sorbitan Sesquioleate.)

The OVA preparations were fed to BDF mice as described in FIG. 1. Subsequently the mice were bled and their serum anti OVA IgG antibody levels determined by ELISA ( Emguall, E., Perlman, P., 1972, "Enzyme Linked lmmunosorbant Assay ELISA III Quantitation of Specific Antibodies by Enzyme Labeled Anti-immunoglobulin in Antigen Coated Tubes," J. Immunol., 109:129). As shown in FIG. 1, oral administration of encapsulated OVA resulted in significant immune response to the specific antigen. Unencapsulated OVA antigens were not immunogenic.

EXAMPLE 2

Properties of Encapsulated OVA

Figure 2:
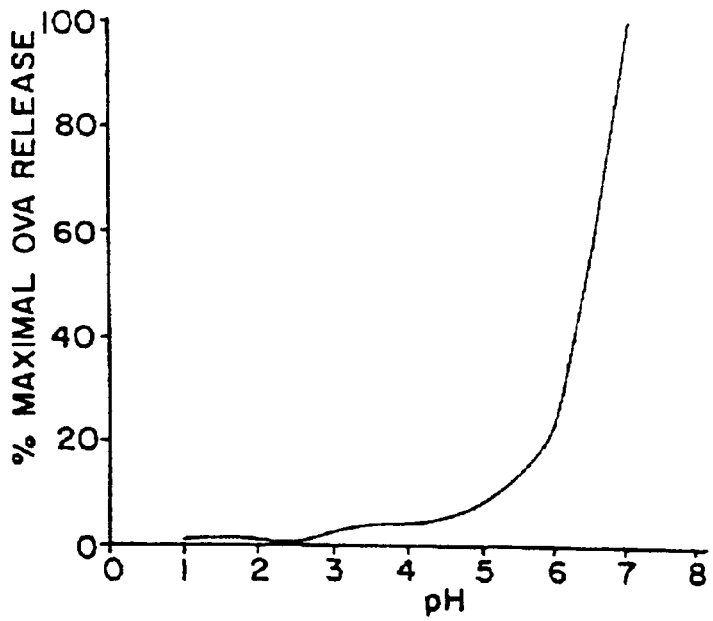
FIG. 2 is a graph depicting the release of hen egg albumin (OVA) from enteric coated microspheres after two hours in solutions at various pH.
Figure 3:
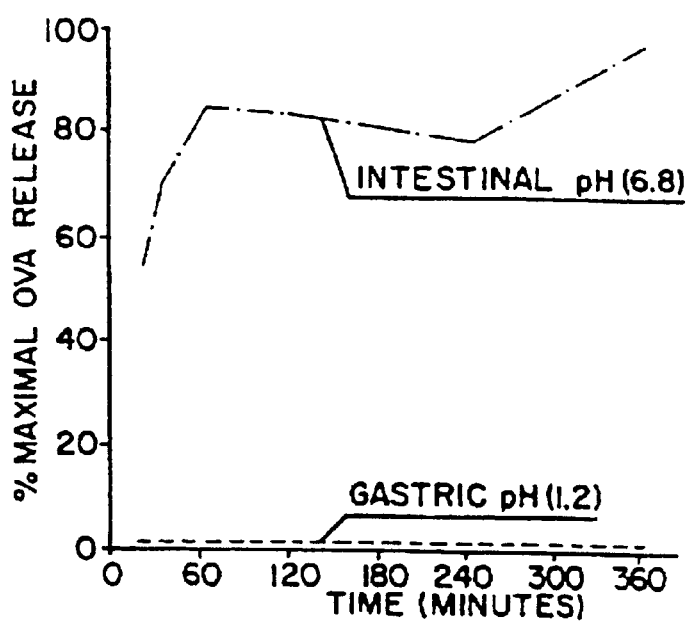
FIG. 3 is a graph depicting OVA released over time from enteric coated microspheres in solutions at gastric (1.2), or intestinal pH (6.8).

OVA coated nonpareils were prepared from 20 grams of nonpareils, 1 gram of OVA, and 1 gram of lactose. These were then coated with Eudragit L30D in a total aqueous system (7 grams Eudragit L30D and 22 grams coated nonpareils). These were initially tested to determine resistance to acid pH typically encountered in the gastric juices. As shown in FIG. 2, the OVA was not released until the pH approached 6. At pH 6 to 7, substantially all of the OVA was released. To determine the release of OVA over time, these microspheres were exposed to either intestinal pH of 6.8 or gastric pH of 1.2 (FIG. 3). At the gastric pH of 1.2, virtually none of the OVA was released for 6 hours. However, at pH 6.8, substantially all of the OVA was released in a short time. OVA released from the microspheres was tested for antigenicity and immunogenicity. It was demonstrated that the released antigen retained its native structure (RAST inhibition assay), and was as immunogenic as the untreated OVA (data not shown). Immune responses to all therapeutic antigens described below were always measured against native antigens by RAST assay, thus proving that the encapsulated antigens retained their native structure.

EXAMPLE 3

Human Studies

1. Preparation of Microspheres With Ragweed

Microencapsulated ragweed microspheres were prepared as follows:

The ragweed solution was formed by dissolving 203 grams of polyvinylpyrrolidone and 203 grams lactose in 2439.6 grams of sterile water (50° C). Next, 34.4 grams of lyophilized short ragweed extract obtained from Greer Laboratories, Lenoir, NC, was added and dissolved at room temperature.

The coating solution was formulated by combining 4068 grams of Eudragit L30D(30% solids) with 122 gram triethyl citrate.

The microspheres were formed in a Glatt model GPCG-5 Wurster spray dryer. The Wurster was set up according to the following specifications:

| Spray Nozzle | |
|---|---|
| Port Size: 1.2 | Atomization air: 20 BAR |
| Port Height: ⅜" | Inlet flap: open |
| Angle: flush | |

The Wurster chamber was loaded with 2000 grams of 30–35 mesh-nonpareils. The inlet air pressure was adjusted such that the microspheres reached a "fluidized" state. The inlet air temperature was increased till the product temperature was between 40–45° C. Spray and atomization-air hoses were connected and the antigen solution was sprayed at a relatively slow rate (10–13 gms/min). The variables of air flow ("outlet flap"), inlet air temperature, and spray rate were adjusted in order to maintain a free "fluidized" state of the microspheres. Throughout the process, the spray rate was gradually increased to the point where it became impossible to achieve a free fluidized state of the particles without raising the product temperature above the desired range (40–45° C.). When all of the antigen solution was sprayed, the spray and atomization hoses were disconnected and the inlet air temperature was decreased to allow the product to cool (37–38° C.). Spray and atomization-air :hoses were reconnected and the enteric coating (Eudragit L30D) was sprayed (initially at around 30 gms/min) again adjusting variables of inlet air temperature and air flow to achieve maximum spray rate while maintaining a product temperature of 29–32° C. At the end of the coating process, spray and atomization-air hoses were disconnected, the inlet air temperature and air flow is adjusted to achieve a product temperature of 55–60° C. and the fluidized particles cured at this temperature for 1h. Following the curing step, the inlet air temperature was decreased and the particles allowed to cool to below 45° C. The finished product was collected and the yield calculated.

The present invention provides an oral treatment modality for a wide variety of conditions. Denaturation of the therapeutic protein is avoided when coating the protein with an enteric coat. Furthermore, the coating provides protection against low pH and enzymatic degradation enabling delivery of the intact molecule into small intestine.

The preceding has been a description of the present invention along with the preferred method currently known of practicing the invention. While there are many minor modifications that can be made without departing from the scope of the present invention, the scope of the present invention should be defined by the appended claims.

What is claimed is:

1. An orally administrable therapeutic composition comprising:
   a therapeutic protein microencapsulated with a water based enteric coating composition wherein said coating composition includes an enteric coating and a solvent consisting essentially of water wherein said protein is a human protein which is not recognized as foreign by the human immune system.

2. The composition claimed in claim 1 wherein said enteric coating composition is a water based emulsion ethylacrylate methacrylic acid copolymer.

3. The composition claimed in claim 2 wherein said therapeutic protein is selected from the group consisting of insulin, human growth factor, myelin basic protein, collagen S antigen, transforming growth factor beta.

4. The method of forming a therapeutic composition comprising:
   forming an aqueous solution containing a therapeutic protein said solution containing no organic solvents;
   microencapsulating said therapeutic protein with an aqueous solution of an enteric coating wherein said aqueous solution of enteric coating contains no organic solvents; and
   wherein said protein is a human protein which is not recognized by the human immune system as foreign.

5. The method claimed in claim 4 wherein said therapeutic protein is maintained at a temperature less-than 50° C.

6. The method claimed in claim 4 wherein said enteric coating comprises an emulsion of an ethylacrylate methacrylic acid copolymer.

7. The method claimed in claim 4 wherein said aqueous solution of therapeutic protein contains a water suspended aluminum composition.

8. The method claimed in claim 7 wherein said aqueous solution contains a stabilizing sugar.

9. The method claimed in claim 8 wherein said sugar is lactose.

10. The composition claimed in claim 1 further comprising a stabilizing sugar.

11. The composition claimed in claim 1 wherein said composition further comprises a water suspended aluminum salt.

\* \* \* \* \*